(12) United States Patent
Pruter

(10) Patent No.: US 6,908,433 B1
(45) Date of Patent: Jun. 21, 2005

(54) ADHESIVE METHOD AND APPARATUS FOR GUIDING NEEDLES

(76) Inventor: Rick L. Pruter, 21 Woodcrest La. NE., Iowa City, IA (US) 52240

(*) Notice: Subject to any disclaimer, the term of this patent is extended or adjusted under 35 U.S.C. 154(b) by 121 days.

(21) Appl. No.: 10/063,753

(22) Filed: May 10, 2002

(51) Int. Cl.[7] ............................................... A61B 8/14
(52) U.S. Cl. ................................................... 600/459
(58) Field of Search ........................... 600/437, 461, 600/439, 459, 471, 464; 128/918; 606/1

(56) References Cited

U.S. PATENT DOCUMENTS

| | | | |
|---|---|---|---|
| 4,567,896 A * | 2/1986 | Barnea et al. | 600/443 |
| 4,742,829 A | 5/1988 | Law et al. | |
| 4,838,506 A * | 6/1989 | Cooper | 248/200 |
| 4,865,590 A * | 9/1989 | Marmar | 604/180 |
| 4,877,033 A * | 10/1989 | Seitz, Jr. | 600/441 |
| 4,883,059 A * | 11/1989 | Stedman et al. | 600/437 |
| 4,911,173 A * | 3/1990 | Terwilliger | 600/464 |
| 5,052,396 A * | 10/1991 | Wedel et al. | 600/461 |
| 5,088,178 A * | 2/1992 | Stolk | 29/453 |
| 5,088,500 A | 2/1992 | Wedel et al. | |
| 5,235,987 A * | 8/1993 | Wolfe | 600/461 |
| 5,469,853 A * | 11/1995 | Law et al. | 600/463 |
| 5,758,650 A * | 6/1998 | Miller et al. | 600/461 |
| 5,910,113 A * | 6/1999 | Pruter | 600/437 |
| 5,941,889 A | 8/1999 | Cermak | |
| 5,968,016 A * | 10/1999 | Yerfino et al. | 604/177 |
| D424,693 S | 5/2000 | Pruter | |
| 6,102,867 A * | 8/2000 | Dietz et al. | 600/461 |
| 6,296,614 B1 | 10/2001 | Pruter | |
| 6,361,499 B1 * | 3/2002 | Bates et al. | 600/461 |
| 6,371,968 B1 * | 4/2002 | Kogasaka et al. | 606/190 |
| 6,475,152 B1 * | 11/2002 | Kelly et al. | 600/461 |

FOREIGN PATENT DOCUMENTS

WO     WO 99/34735     7/1999

OTHER PUBLICATIONS

"*Solutions for Ultrasound*" brochure from CIVCO Medical Instruments Co., Medical Parkway, 102 Highway 1 South, Kalona, Iowa 52247.

* cited by examiner

*Primary Examiner*—Ali Imam
(74) *Attorney, Agent, or Firm*—Simmons, Perrine, Albright & Ellwood, PLC

(57) ABSTRACT

An apparatus and method for guiding a needle where a structure is attached to the sterile sheath to aid in coupling the needle guide to the transceiver. In one case, the needle guide is attached to the exterior of the sheath; in another, a needle guide adapter is attached to the exterior of the sheath; in still another, an adhesive is attached on the inside of the sheath to assist in attachment with the transceiver. In still another, a temporary adhesive cover is attached to the internal adhesive and is removable upon full insertion of the transceiver into the sheath.

20 Claims, 3 Drawing Sheets

ADHESIVE METHOD AND APPARATUS FOR GUIDING NEEDLES

BACKGROUND OF INVENTION

In recent years, handheld medical imaging transceivers, such as ultrasound and gamma ray transceivers, have been used extensively for various medical imaging situations. Many clinics will use multiple transceivers. Some handheld transceivers are designed for external use, while trans-rectal and trans-vaginal transceivers are designed for use within body cavities.

In the past, each type of transceiver may require a different needle guide and/or a different mounting bracket to which a needle guide is attached. With numerous transceivers and numerous needle guide brackets, a medical imaging professional may become confused and frustrated as to what needle guide goes with which bracket and which transceiver, thereby reducing the efficiency of operations of the clinic.

Consequently, there exists a need for improved methods and apparatus for guiding needles in an efficient manner.

SUMMARY OF INVENTION

It is an object of the present invention to provide an apparatus and method for guiding a needle in an efficient manner.

It is a feature of the present invention to utilize a sterile sheath with an internal adhesive for affixing to a transceiver.

It is another feature of the present invention to include a removable internal adhesive cover inside said sterile sheath to facilitate ease of insertion of a medical imaging transceiver therein.

It is another feature of the present invention to include a sterile sheath with a needle guide attached thereto.

It is another feature of the present invention to include a needle guide adapter bracket attached to the sterile sheath.

It is an advantage of the present invention to achieve improved efficiency in guiding needles.

The present invention is an apparatus and method for guiding needles designed to satisfy the aforementioned needs, provide the previously stated objects, include the above-listed features, and achieve the already articulated advantages. The present invention is carried out in a "technician burden-less" manner in a sense that the burden on a medical imaging of coupling one of a multiple of needle guides with one of a multiple of mounting brackets for one of a multiple of transceivers, has been greatly reduced.

Accordingly, the present invention is an apparatus and method including a sterile sheath which has a structure coupled thereto for assisting in affixing a needle guide to a transceiver.

BRIEF DESCRIPTION OF DRAWINGS

The invention may be more fully understood by reading the following description of the preferred embodiments of the invention, in conjunction with the appended drawings wherein.

DETAILED DESCRIPTION

Figure 1:
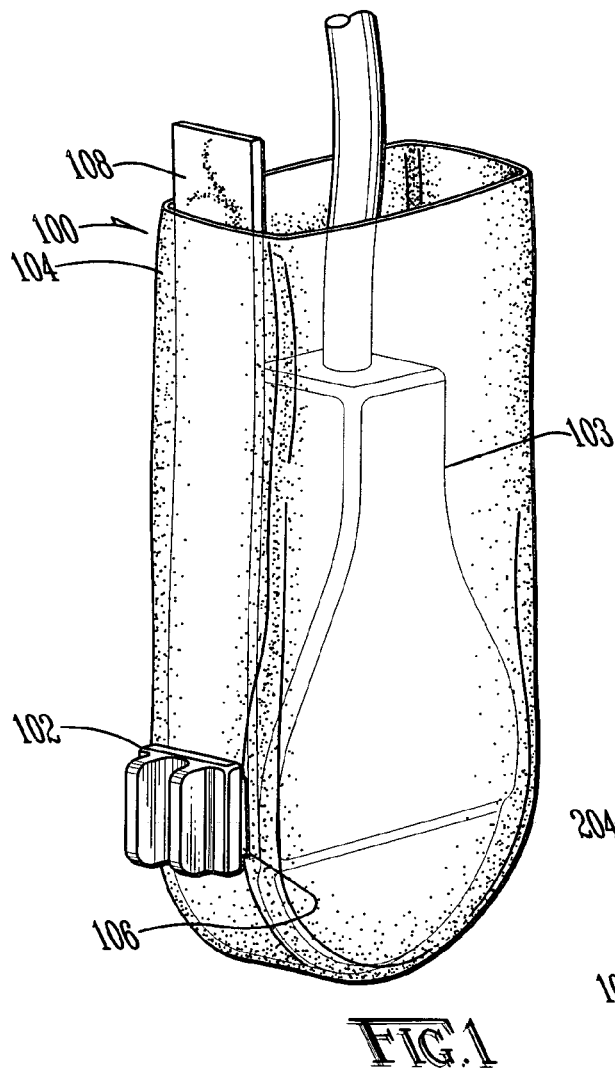
FIG. 1 is a perspective view of the present invention prior to attachment to a transceiver.

Now referring to the drawings wherein like numerals refer to like matter throughout, and more specifically referring to FIG. 1, there is shown a needle guide/transceiver assembly 100 of the present invention, which includes a needle guide 102. Needle guide 102 is coupled to medical imaging device 103, which could be an ultrasound transducer, gamma ray transceiver or other imaging device. Needle guide 102 is preferably a plastic material, such as ABS or equivalent; however, other materials, such as aluminum, surgical steel, and any other suitable material could be substituted. Needle guide 102 is coupled to sterile sheath 104 by exterior adhesive 106. Sterile sheath 104 can be a latex sheath or other material known for use with sheaths and sterile sheaths for medical imaging transceivers. Exterior adhesive 106 can be a contact adhesive applied to sterile sheath 104 or needle guide 102 or it may be adhesive tape. It should be understood that the exterior adhesive 106 can be replaced with an ultrasonic weld or any similar means of attaching matter to a sheath.

Figure 2:
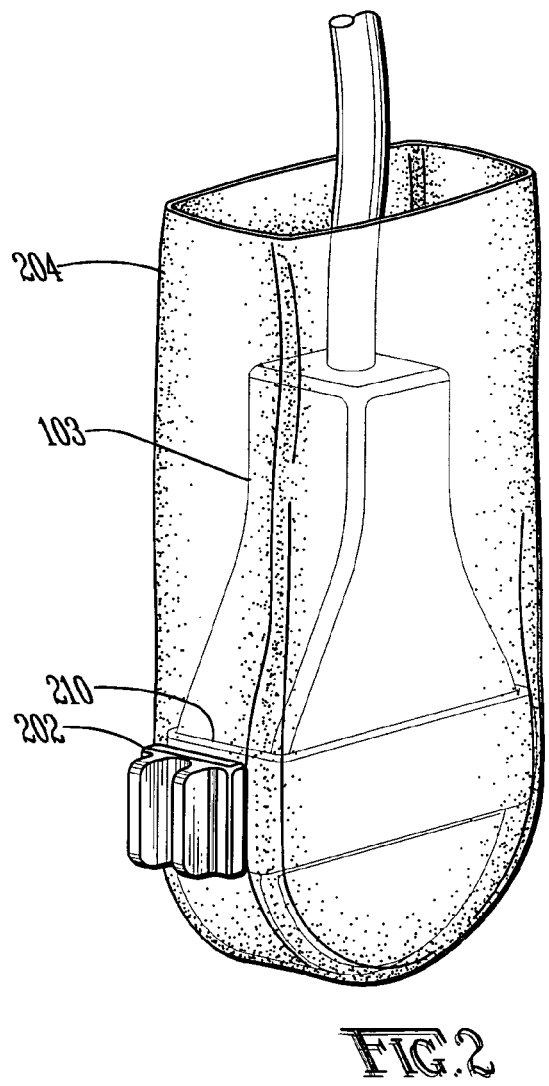
FIG. 2 is a perspective view of an alternate embodiment of the present invention which includes a bracket disposed on the transceiver.

Now referring to FIG. 2, there is shown a needle guide assembly of the present invention, having a needle guide 202 coupled through a sterile sheath 204 to a transceiver mounting bracket 210 disposed on a medical imaging device 103.

Figure 3:
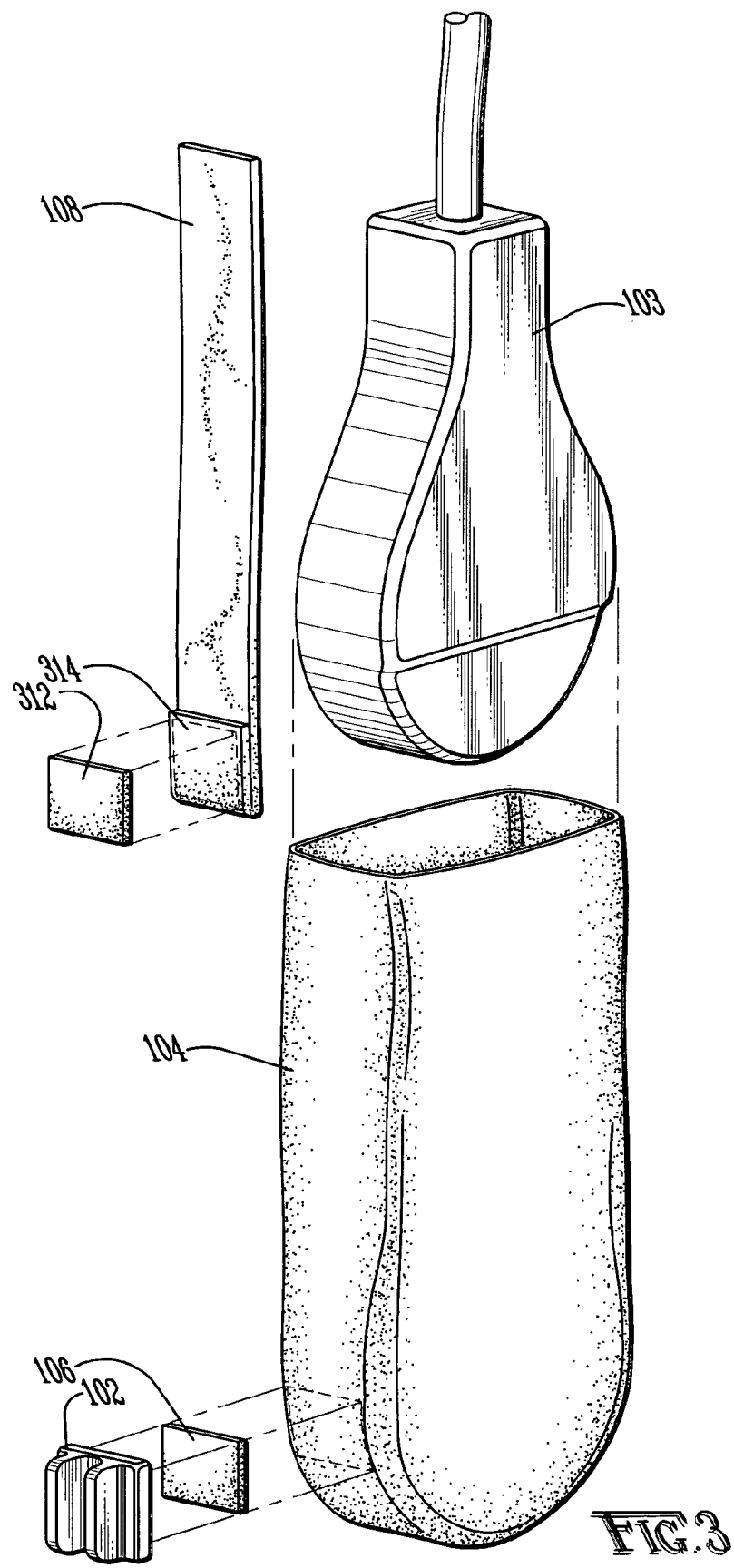
FIG. 3 is a partially exploded perspective view of the apparatus of FIG. 1.

Now referring to FIG. 3, there is shown an exploded view of the needle guide system of FIG. 1, which includes an internal adhesive material 312 disposed on the inside of sterile sheath 104. Internal adhesive material 312 is disposed adjacent to, but on opposing sides of, sterile sheath 104 from exterior adhesive 106. Internal adhesive material 312 is covered by cover for internal adhesive material 314. Cover for internal adhesive material 314 is shown as an integral part of elongated adhesive cover removing pull 108. In a preferred embodiment, elongated adhesive cover removing pull 108 is a strip of material which is folded over at the bottom end to form cover for internal adhesive material 314. It should be understood that cover for internal adhesive material 314 and elongated adhesive cover removing pull 108 need not be integral, nor need they be the same material.

Figure 4:
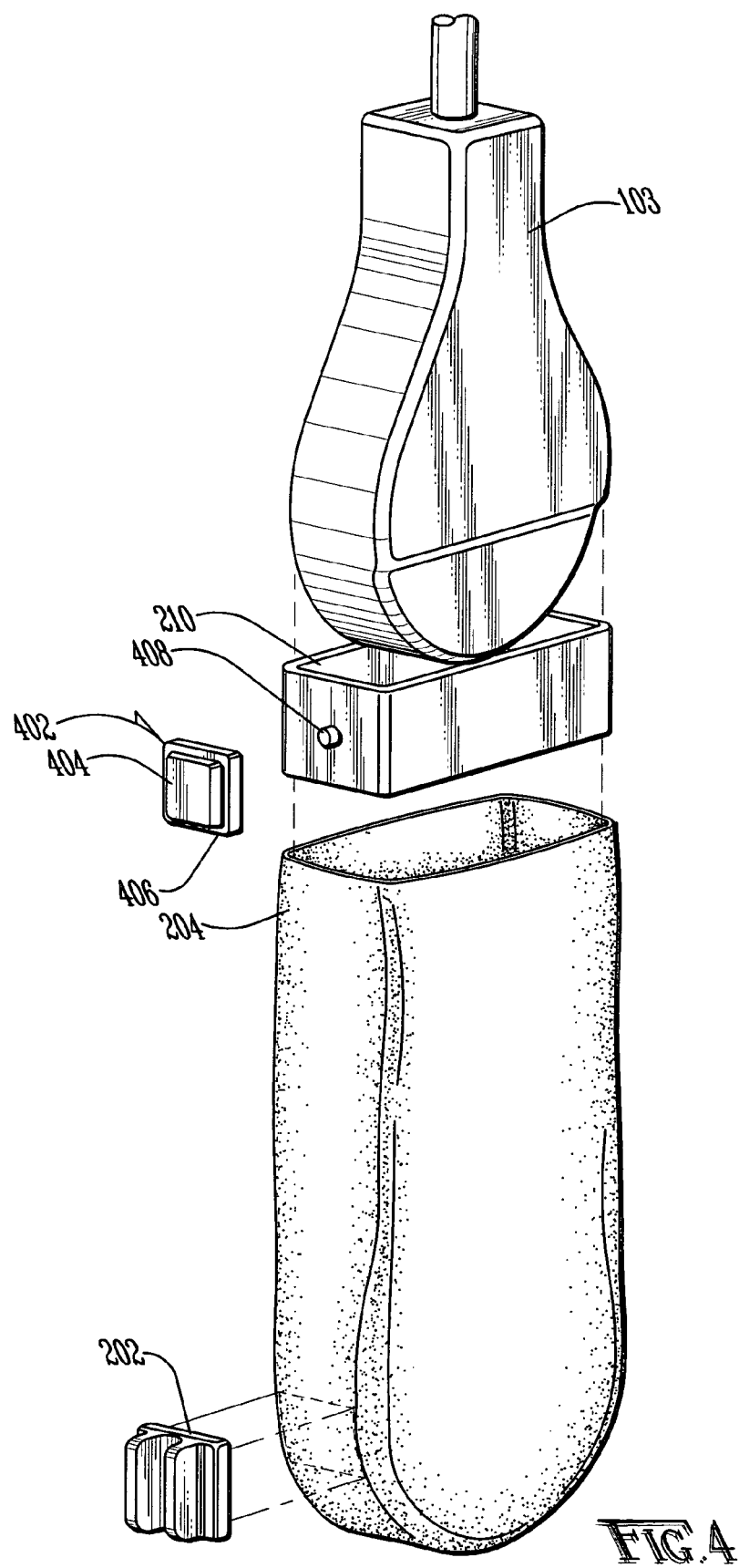
FIG. 4 is a partially exploded perspective view of an alternate embodiment of the needle guide of FIG. 2.

Now referring to FIG. 4, there is shown an adapter 402 having a protruding central portion 404 and non-protruding area 406. Adapter 402 can be attached to sterile sheath 204 in a manner similar to the way needle guide 102 is attached to sterile sheath 104. Adapter 402, after it has been affixed to sterile sheath 204, may be coupled to transceiver mounting bracket 210 by mating with a surface structure 408 disposed on transceiver mounting bracket 210.

In operation, the apparatus and method of the present invention as described and shown in FIGS. 1 and 3, could function as follows:

Medical imaging device 103 is inserted into sterile sheath 104. Elongated adhesive cover removing pull 108 is pulled to expose internal adhesive material 312. Internal adhesive material 312 is then pressed against medical imaging device 103. Needle guide 102, which has been previously attached to sterile sheath 104 via exterior adhesive 106 or other means, can be used for normal clinical activities.

With respect to the embodiment of the present invention shown in FIGS. 2 and 4, the system could function as follows:

Transceiver mounting bracket 210 is mounted on medical imaging device 103. The medical imaging device 103 is inserted into sterile sheath 204. Adapter 402, which has been previously mounted on sterile sheath 204 as discussed above, is mated to surface structure 408. Adapter 402, with its protruding central portion 404 and non-protruding area 406, then can be mated with needle guide 202, thereby coupling needle guide 202 with medical imaging device 103.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

While the figures and the detailed description herein are focused upon a general-purpose abdominal transceiver, it is intended that the present invention be read to include within the claims endo-cavity transceivers and any other medical imaging device irrespective of its manner of use.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

What is claimed is:

1. An improved needle guiding apparatus for use with a medical imaging transceiver assembly, the needle guiding apparatus comprising:
    a sheath having an opening configured at a top end for receiving a medical imaging transceiver and a closed opposing end;
    said sheath not having said medical imaging transceiver disposed therein;
    matter, attached to an exterior portion of said sheath at a location on said sheath other than said top end, configured and positioned to assist in at least indirectly guiding a needle with respect to said medical imaging transceiver when said medical imaging transceiver is later disposed within said sheath.

2. A needle guiding apparatus of claim 1 further comprising an adhesive on an interior surface of said sheath.

3. A needle guiding apparatus of clam 2 further comprising:
    a temporary adhesive cover disposed over said adhesive; and,
    means for removal of the temporary adhesive cover.

4. A needle guiding apparatus of claim 3 further comprising an adapter configured for cooperation with a needle guide.

5. A needle guiding apparatus of claim 3 further comprising a needle guide coupled to said sheath.

6. A needle guiding apparatus of claim 5 further comprising an ultrasonic weld disposed between and bonding said sheath with said needle guide.

7. A needle guiding apparatus of claim 4 further comprising an adhesive disposed between and bonding said adapter and said sheath.

8. A needle guiding apparatus of claim 4 further comprising tape disposed between and bonding said adapter and said sheath.

9. A needle guiding apparatus of claim 1 wherein said matter is an adapter configured for cooperation with a needle guide.

10. A needle guiding apparatus of claim 1 wherein said matter is a needle guide.

11. A needle guiding apparatus of claim 10 wherein said needle guide has a mating structure thereon configured for mechanically coupling with mounting structure on said medical imaging transceiver.

12. A needle guiding apparatus of claim 11 wherein mounting structure is a portion of a mounting bracket configured for mounting on said medical imaging transceiver.

13. A method of coupling a medical instrument guide to a medical imaging transceiver comprising the steps of:
    providing a medical imaging transceiver;
    providing a sheath with an opening at a top end and having a closed bottom end and with matter disposed thereon, on an external surface at a location other than at said top end;
    inserting said medical imaging transceiver into said opening at said top end sheath;
    coupling said sheath with said medical imaging transceiver; and,
    using said matter to assist in guiding a medical instrument with respect to said medical imaging transceiver.

14. A method of claim 13 wherein said step of using said matter further comprises the step of: coupling a needle guide to an adapter affixed to an exterior of said sheath.

15. A method of claim 13 wherein said step of coupling said sheath further comprises pressing an adhesive affixed to said sheath onto said medical imaging transceiver.

16. A method of claim 13 wherein said step of coupling said sheath her comprises the step of mating a portion of said matter with a portion of structure on said medical imaging transceiver.

17. A method of coupling a needle guide to a medical imaging transceiver comprising the steps of:
    providing a medical imaging transceiver;
    providing a sheath with matter disposed thereon, on an external surface;
    inserting said medical imaging transceiver into said sheath;
    coupling said sheath with said medical imaging transceiver;
    using said matter to assist in guiding a needle with respect to said medical imaging transceiver;
    wherein said step of coupling said sheath further comprises pressing an adhesive affixed to said sheath onto said medical imaging transceiver; and
    wherein said step of pressing an adhesive is preceded by a step of removing a temporary adhesive cover from inside said sheath by pulling an elongated member extending through a top opening in said sheath.

18. A method of coupling a needle guide to a medical imaging transceiver comprising the steps of:
    providing a medical imaging transceiver;
    providing a sheath with matter disposed thereon, on an external surface;
    inserting said medical imaging transceiver into said sheath;
    coupling said sheath with said medical imaging transceiver;
    using said matter to assist in guiding a needle with respect to said medical imaging transceiver;
    wherein said step of coupling said sheath further comprises pressing an adhesive affixed to said sheath onto said medical imaging transceiver; and wherein said step of using said matter further comprises the step of coupling a needle guide to an adapter affixed to an exterior of said sheath.

19. A medical imaging system comprising:

a sterile sheath having a first end with an opening therein for receiving therethrough a medical imaging transceiver;

said sterile sheath having a closed second end;

an adhesive material, disposed at a first location of and on an inside surface of said sterile sheath;

a cover, configured to inhibit attachment of said adhesive material to said medical imaging transceiver, while said medical imaging transceiver is being inserted into said sterile sheath;

an elongated pull disposed inside said sterile sheath and attached to said cover, said elongated pull being configured to facilitate removal of said cover from said adhesive while said medical imaging transceiver is disposed in said sterile sheath;

an adapter disposed at said first location and coupled to an exterior surface of said sterile sheath;

an ultrasonic weld disposed between and coupling said adapter with said exterior surface of said sterile sheath;

a needle guide coupled to said adapter;

said needle guide having a first male/female component of a mechanical mating assembly; and, said adapter having a second male/female component which mates with said first male/female component when said needle guide is engaged with said adapter.

20. A medical imaging system of claim 19 further comprising an ultrasound transducer.

* * * * *

UNITED STATES PATENT AND TRADEMARK OFFICE
CERTIFICATE OF CORRECTION

PATENT NO. : 6,908,433 B1
DATED : June 21, 2005
INVENTOR(S) : Rick L. Pruter

It is certified that error appears in the above-identified patent and that said Letters Patent is hereby corrected as shown below:

Column 4,
Line 31, please delete the word "her" and insert therefor -- further --.

Signed and Sealed this

Eleventh Day of October, 2005

JON W. DUDAS
*Director of the United States Patent and Trademark Office*